United States Patent [19]

Mariotti et al.

[11] Patent Number: 5,091,510
[45] Date of Patent: Feb. 25, 1992

[54] RETRO-INVERSO ANALOGUES OF THYMOPENTIN, AND THEIR USE IN THE PREPARATION OF PHARMACEUTICAL COMPOSITIONS

[75] Inventors: Sabina Mariotti, Fara Sabina; Alessandro Sisto, Rome; Luciano Nencioni, Poggibonsi; Luigi Villa, Florence; Antonio S. Verdini, Monterotondo, all of Italy

[73] Assignee: Scalvo, S.p.A., Siena, Italy

[21] Appl. No.: 454,282

[22] Filed: Dec. 21, 1989

[30] Foreign Application Priority Data

Dec. 23, 1988 [IT] Italy .................. 23099 A/88

[51] Int. Cl.$^5$ .................. C07K 7/06; A61K 37/02
[52] U.S. Cl. ..................... 530/330; 530/321
[58] Field of Search ............ 514/17, 11; 530/321, 530/330

[56] References Cited

U.S. PATENT DOCUMENTS 4,505,853  3/1985  Goldstein et al. ............ 260/112.5 R
4,547,489 10/1985  Goldstein et al. ............ 514/11
4,629,723 12/1986  Goldstein et al. ............ 514/17

FOREIGN PATENT DOCUMENTS 0282891  9/1988  European Pat. Off.

OTHER PUBLICATIONS

Heavner et al., Peptides, vol. 7, pp. 1015-1019 (1986.

Denes et al., Chemical Abstracts, vol. 107, No. 23, (1987) p. 211960d.

Primary Examiner—Lester L. Lee
Assistant Examiner—A. Davenport
Attorney, Agent, or Firm—Hedman, Gibson & Costigan

[57] ABSTRACT

New analogues of thymopentin (TP5) and of its tetrapeptide fragment (TP5$^{1-4}$) containing two non-contiguous retro-inverted bonds in the peptide chain are described.

The new compounds, of general formula (I)

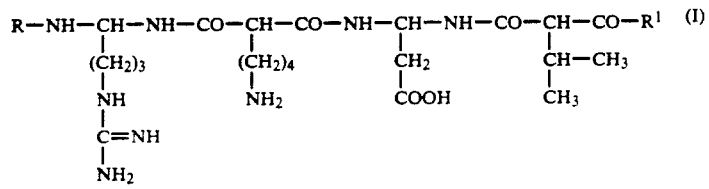

where
R is hydrogen or an acyl radical, and
R$^1$ is an —OR$^2$ group or an

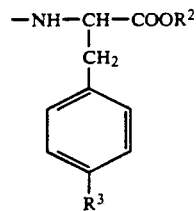

group where R$^2$ is a hydrogen atom or a hydrocarbon radical, and R$^3$ is a hydrogen atom or a hydroxyl group, and the corresponding pharmaceutically acceptable salts of acid or basic addition, possess immunomodulating activity.

8 Claims, No Drawings

RETRO-INVERSO ANALOGUES OF THYMOPENTIN, AND THEIR USE IN THE PREPARATION OF PHARMACEUTICAL COMPOSITIONS

This invention relates to new analogues of thymopentin (TP5) and its tetrapeptide fragment (TP5[1-4]), containing in the peptide chain two retro-inverted bonds, the process for preparing these new compounds and their use in pharmaceutical formulations. In particular, the present invention firstly relates to analogues of thymopentin and its tetrapeptide fragment (TP5[1-4]) having the following general formula (I)

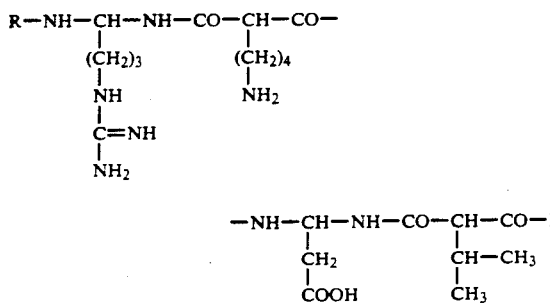

where
R is hydrogen or an acyl radical, and
R[1] is an —OR[2] group or an

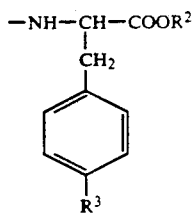

group where
R[2] is a hydrogen atom or a $C_1$-$C_6$ linear or branched chain alkyl radical, a $C_3$-$C_6$ linear or branched chain alkenyl or alkynyl radical, or a $C_7$-$C_{12}$ aryl-alkyl or alkyl-aryl radical, and
R[3] is a hydrogen atom or a hydroxyl group, and the corresponding pharmaceutically acceptable salts of acid or basic addition.

The new compounds of the present invention as heretofore defined by their distinguishing chemical structural formula can be indicated more concisely using the symbols internationally recognised in the peptide field, as:

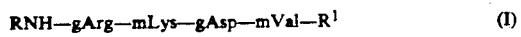

RNH—gArg—mLys—gAsp—mVal—R[1] (I)

where
R is hydrogen or an acyl radical, and
R[1] is an —OR[2] group or a —Tyr—OR[2] or —Phe—OR[2] group where
R[2] is a hydrogen atom or a radical as heretofore defined.

In this latter formula, gArg indicates a geminal diamino residue derivable from the amino acid arginine by replacing the carboxyl with an amino group, and mLys indicates a malonyl residue substituted in position 2- with the side chain of the amino acid lysine.

Likewise, gAsp indicates a geminal diamino residue derivable from aspartic acid by replacing the carboxyl with an amino group, and mVal indicates a malonyl residue substituted in position 2- with the side chain of the amino acid valine.

Finally, Tyr and Phe represent the tyrosine and phenylalanine residues respectively.

For the purposes of the present invention the term "acyl radical" signifies those acyl radicals deriving from $C_1$-$C_6$ linear or branched chain alkanoic acids such as formyl, acetyl, propionyl, succinoyl etc., and those aromatic acyl radicals deriving from benzoic and substituted benzoic acid such as benzoyl, 4-nitrobenzoyl, 2,3,4-trimethoxybenzoyl etc.

As used herein, the term "pharmaceutically acceptable salts" indicates those salts of acid or basic addition in which, respectively, the anion or cation is relatively non-toxic and innocuous when the compounds are administered in the form of salts of addition at therapeutically effective doses, so that any side effects of the anions or cations do not cancel the beneficial effects of the active principle.

Acids able to form pharmaceutically acceptable salts of acid addition with the compounds of formula (I) include for example inorganic acids such as hydrochloric acid, hydrobromic acid, phosphoric acid, sulphuric acid etc., organic carboxylic acids such as formic acid, acetic acid, propionic acid, lactic acid, malonic acid, succinic acid etc., and organic sulphonic acids such as methanesulphonic acid and naphthalenesulphonic acid.

Bases able to form pharmaceutically acceptable salts with the compounds of formula (I) include for example mineral bases such as sodium hydroxide, potassium hydroxide, ammonium hydroxide etc., and organic bases such as triethylamine, triethanolamine etc. These salts of addition can either be obtained directly via the synthesis process for the new retro-inverso peptides, or be prepared by conventional methods starting from compounds of formula (I), in the form of free bases or acids, by treating with one or more equivalents of the chosen acid or base.

If desired, a given salt of acid addition can be converted into another by treating the former with a suitable ion exchange resin as described for example by R. A. Boissonas et al. in Helv. Chim. Acta, 43, 1349 (1960).

A preferred group of compounds of the present invention comprises those compounds of formula (I) in which R represents a hydrogen atom, or a metabolically labile acyl radical, or an acyl radical of which the bond to the amino group is rapidly cleaved during the initial stages of the metabolic path of the product and which does not have toxic effects or controindications in therapy when used in a concentration in which the compound of formula (I) provides the desired pharmacological effect, R[1] is as heretofore defined and R[2] is hydrogen.

A more preferred group of compounds comprises those compounds of formula (I) in which R is a hydrogen atom, R[1] is as heretofore defined and R[2] is hydrogen.

A still more preferred group of compounds comprises those compounds of formula (I) in which
R is a hydrogen atom and
R[1] is a

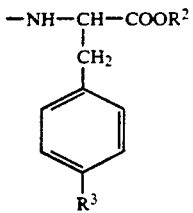

group where
R² is a hydrogen atom and
R³ is as heretofore defined. The compounds of the present invention have demonstrated considerable activity on the immune system.

In the last fifteen years G. Goldstein and his group have studied in detail the biological action and the possible pharmacological use of a polypeptide hormone secreted by the epithelial cells of the thymus, namely thymopoietin [G. Goldstein, Nature, 247, 11 (1974); D. H. Schlesinger et al., Cell, 5, 361 (1975); T. Audhya et al. Biochemistry, 20, 6195 (1981)], the primary sequence of which comprises 49 amino acids.

Thymopoietin performs various regulatory actions in the body, influencing neuromuscular transmission [G. Goldstein, Lancet, 2, 119 (1968)], differentiation between T and B lymphocytes [M. P. Scheid et al., J. Exp. Med., 147, 1727 (1978)], and the immune response [C. Y. Lau et al., J. Immunol., 125, 1634 (1980)].

Structure-activity studies have shown that the entire 49 amino acid sequence of thymopoietin is not required for the biological activity, in that the pentapeptide H—Arg—Lys—Asp—Val—Tyr—OH (Thymopentin, TP5) corresponding to the amino acid sequence 32-36 possesses the entire biological activity of the natural hormone both in vitro and in vivo [G. Goldstein et al., Science, 204, 1309 (1979)].

Thymopentin has already been clinically introduced, both in the treatment of diseases of autoimmune origin such as rheumatoid arthritis, and as a stimulant for the body defence system in the treatment for example of primary immunodeficiency, due to the absence or incomplete development of the thymus and consequent alteration in the maturation of the T lymphocytes and of the acute or recurrent viruses, or as an aid in vaccination.

Setting up the therapeutic protocol is made critical by the difficulty in determining the effective dose, in that the pharmacological effect can vary considerably according to the method and duration of administration [T. Audhya et al., Surv. Immunol. Res., 4th suppl., 1, 17 (1985); and T. Audhya et al., Int. J. Peptide Protein Res., 22, 568 (1983)].

The limiting example is that reported by Bolla et al. in Int. J. Clin. Pharm. Res., IV(6), 431 (1984), according to which the stimulating effect on the production of antibodies by TP5 when administered subcutaneously is totally suppressed if the same dose is administered intravenously. A possible cause of this is the short half-life of TP5 in the plasma. In this respect, TP5 is rapidly degraded in the plasma ($t_{\frac{1}{2}} = 1.5$ min) by the action of various proteases [T. P. Tischio et al., Int. J. Peptide Protein Res., 14, 479 (1979)]

Intense research has been carried out in recent years for the purpose of obtaining TP5 analogues with increased resistance to proteases. Mention can be made for example of European patent application EP-A-135722 and U.S. Pat. No. 4,505,853 relative to thymopentin analogues obtained by suitably varying the individual amino acids within the peptide sequence.

Again for this purpose, analogues of thymopentin and of the tripeptide fragment ($TP^{1-3}$) have recently been synthesized in which the most labile of the bonds in the peptide chain, i.e. the bond between the arginine residue and the lysine residue [see J. P. Tischio et al., Int. J. Peptide Protein Res. 14, (1979), pp 479–484, and in particular FIG. 4] has been suitably retro-inverted. The compounds obtained in this manner, which have maintained if not improved the immunomodulating activity of thymopentin and its fragment, have proved much more stable than the corresponding non-retroinverted compounds towards peptidase. In particular, for example whereas the half life for thymopentin in heparinized human plasma is 1.5 minutes, that of the analogue retro-inverted at the Arg-Lys bond under the same experimental conditions is 22 minutes. Although this is a considerable improvement, it is also apparent that if compounds with the pharmacological possibilities of thymopentin but with increasingly long half lives were available, the therapeutic use of thymopentin could be rationalized to the maximum extent.

It has now been surprisingly found that by inverting not only the bond between the arginine and the lysine but also the bond between the aspartic acid and the valine, products are obtained which although maintaining the immunomodulating activity spectrum of thymopentin, are practically refractory to enzymatic demolition. For example, the thymopentin analogue in which the two Arg-Lys and Asp-Val bonds have been retro-inverted (the compound of Example 1), when tested for stability to enzymatic hydrolysis in heparinized human plasma in parallel with thymopentin and with thymopentin retro-inverted only at the Arg-Lys bond, showed a half life of more than 5 hours. This result is even more surprising considering that in the natural peptide the cleavage of the Asp-Val bond is of little importance (see J. P. Tischio et al., the aforesaid reference and in particular FIG. 4 which shows the possible degradation scheme of thymopentin in the plasma, and where Asp-Val cleavage never appears), whereas evidently this cleavage becomes crucial in the retro-inverted analogue.

The compounds of the present invention are conveniently prepared by condensing a fragment of formula (II)

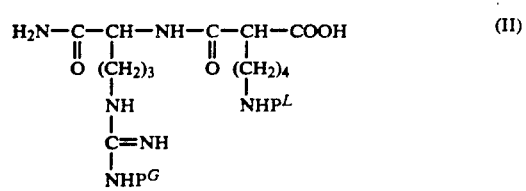

where
$P^L$ indicates a protecting group for the side chain amino function, and
$P^G$ indicates a suitable protecting group for the guanidino function,
with a fragment of formula (III)

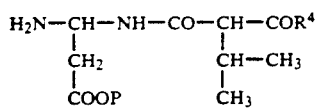

where

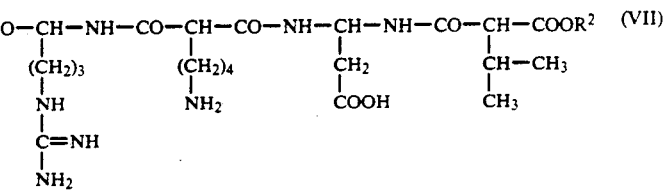

—Tyr—OR² group in that the phenolic hydroxyl of the tyrosine is extremely sensitive to TIB and must be protected during the amide/amine conversion step.

Thus if a compound of formula (I) is required in which R¹ is a —OR² group, unblocking the protecting groups before the amide/amine conversion by the TIB will lead to an intermediate of formula (VII)

$$H_2N-CO-CH-NH-CO-CH-CO-NH-CH-NH-CO-CH-COOR^2 \quad (VII)$$
with side chains: $(CH_2)_3$—NH—C(=NH)—NH_2; $(CH_2)_4$—NH_2; $CH_2$—COOH; $CH$—CH_3 with CH_3

R⁴ is a —OR² group in which R² is as heretofore defined, a —OP group where P is a protecting group for the carboxyl function, or a group of formula (IV)

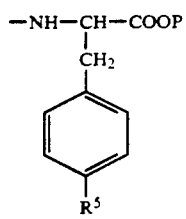

where
P is as heretofore defined, and
R⁵ is a hydrogen atom or a —OP^J group where P^J is a protecting group for the hydroxyl function of the tyrosine, followed by conversion of the terminal amido group of the obtained intermediate of formula (V)

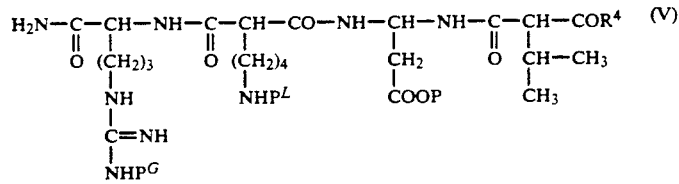

into a primary amino group by treatment with 1,1-bis-trifluoroacetoxy-iodobenzene (TIB) to give an intermediate of formula (VI)

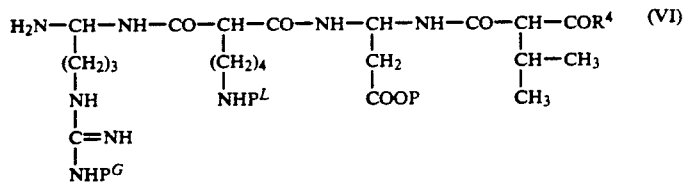

followed by possible acylation of the terminal amino function formed, and the removal of the protecting groups.

If a compound of formula (I) is required in which R is hydrogen and R¹ is a —OR² group, the order of the steps involved in conversion of the amide to primary amine and the deprotection can be conveniently reversed. This is however not possible if a compound of formula (I) is to be obtained in which R¹ represents the which is reacted with the 1,1-bis-trifluoroacetoxy-iodobenzene to give the required retro-inverso peptide of formula (I).

Consequently, the present invention also provides the intermediate compounds of formulas (V), (VI) and (VII) which are obtained during the synthesis of the pharmacologically active products of formula (I).

In greater detail, the first step of the aforesaid reaction scheme can be conveniently effected by any of the methods known in the literature for peptide synthesis. Excellent results in terms of yield and product purity have been obtained using a carbodiimide such as dicyclohexylcarbodiimide or diisopropylcarbodiimide and 1-hydroxybenzotriazole. Specifically the reaction is effected by adding a slight excess of the 1-hydroxybenzotriazole to a solution of the acid of formula (II) maintained at low temperature, followed by adding the dicyclohexyl- or diisopropyl-carbodiimide, and then the reaction partner of formula (III).

For this condensation reaction, which can be conveniently carried out at ambient temperature, conventional aprotic polar organic solvents able to solubilize the reactants and not interfere negatively with the progress of the reaction are used. Selected solvents are dimethylformamide, acetonitrile and dimethylsulphoxide, possibly mixed with less polar solvents such as halogenated aliphatic hydrocarbons, eg. methylene chloride, dichloroethane etc.

Protecting groups which can be conveniently used in this synthesis are the conventional groups known in the literature and commonly used in classical peptide synthesis. In particular, P^L is preferably a tert-butoxy-carbonyl group or benzyloxycarbonyl group, possibly nitro- or halo-substituted; $P^G$ is preferably a benzenesulphonyl group variously substituted, such as an alkylbenzenesulphonyl group, eg. toluenesulphonyl, or an alkylalkoxybenzenesulphonyl group, eg. 4-methoxy-2,3,6-trimethylbenzenesulphonyl; $P^J$ is preferably a tert-butyl or tert-amyl group in that such groups have proved stable to the action of TIB; and finally P can be any protecting group for the terminal carboxyl functions, such as an alkyl group, eg. tert-butyl or tert-amyl, or an arylalkyl group, eg. benzyl or substituted benzyl.

When the condensation reaction, the progress of which can be easily followed by TLC, is complete, the product obtained is recovered by conventional methods.

In particular, according to a preferred aspect, if using a carbodiimide as coupling agent the product is recovered by filtering off the urea which forms, evaporating the solvent, washing the residue or a solution of the residue in a suitable organic solvent with weakly basic and weakly acid solutions, and finally purifying the product by crystallization or chromatography.

The product obtained in this manner is then reacted with 1,1-bistrifluoroacetoxy-iodobenzene (TIB) by the method described in U.S. patent application Ser. No. 448,831, by which the amide substrate is reacted with a slight excess of TIB in an aqueous mixture of an inert solvent such as dimethylformaldehyde, acetonitrile, etc. The reaction is effected by bubbling an inert gas, typically nitrogen, into the reaction mixture and monitoring its progress by TLC. When complete conversion of the amide into amine is noted, the organic solvent is removed and the product easily recovered by lyophilization. If desired the product obtained in this manner can then be acylated using active esters of the acid R—OH, such as the p-nitro-phenyl ester, the 2,4,5-trichloro-phenyl ester etc. The deprotection step is then effected by methods known in this field. In general, if conventional protecting groups are used, such as tert-butyl or tert-amyl for the carboxyl and hydroxyl of the tyrosine, the tert-butoxycarbonyl or benzyloxycarbonyl groups for the amino group of the lysine, and the benzenesulphonyl groups for the guanidino group of the arginine, these are conveniently removed by acidolysis in an acid medium such as with dilute hydrochloric acid in acetic acid, with trifluoroacetic acid or with a mixture of trifluoroacetic acid and trifluoromethanesulphonic acid, in the presence of a small percentage of ethanedithiol, anisole, thioanisole or resorcinol used as scavengers to trap the carbocations which form. After termination of the deprotection step the desired product of formula (I) is recovered either as such or as the salt of addition, and is then purified by conventional methods.

If a compound of formula (I) is required in which R is a hydrogen atom and $R^1$ is a $-OR^2$ group, as stated, the order of the amide/amine conversion and deprotection steps is preferably reversed.

The general methods for their implementation are however unchanged.

The obtained compounds of formula (I) are tested for homogeneity by TLC and HPLC, and for purity by amino acid analysis and NMR. The starting compounds of formula (II) and (III) can be easily prepared either from commercially available compounds or from compounds prepared for the purpose by known methods in the field of peptide and organic synthesis.

In particular, the fragment of formula (II) can be conveniently prepared from an amide of formula (VIII)

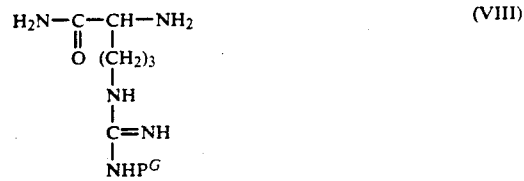

where $P^G$ is a protecting group for the guanidino function, and a hemiester of the 2-substituted malonic acid of formula (IX)

where $P^L$ is a suitable protecting group for the amino function, following the known peptide condensation methods.

The compound of formula (VIII) is prepared by forming the amide from the corresponding amino acid suitably protected both at the guanidino group and at the amino group, then unblocking the amino group, while the compound of formula (IX) is prepared from diethyl malonate by inserting the substituting group in the 2-position followed by partial hydrolysis. The fragment of formula (III) is also conveniently prepared by condensing an amide of formula (X)

where P is a protecting group for the carboxyl function, with a compound of formula (XI)

where $R^4$ is as heretofore defined, then converting the amide to primary amine with TIB.

The compound of formula (XI) where $R^4$ is a group of formula (IV) can be prepared, in accordance with schemes known in the literature, from the hemiester of the 2-substituted malonic acid of formula (XII)

and a compound of formula (XIII)

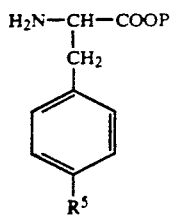

(XIII)

where P and $R^5$ have the aforesaid meanings.

Alternatively, as illustrated in the patent application filed on the same date by the present applicant, instead of using a malonic acid derivative of formula (IX) or (XII), a compound of formula (XIV)

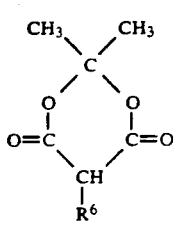

(XIV)

can be used where $R^6$ is a $-(CH_2)_4-NHP^L$ or $-CH(CH_3)CH_3$ group respectively, and effecting the condensation with the amide of formula (VIII) or (X), or with the compound of formula (XIII), in the presence of a suitable sylanizing agent.

The compounds of the present invention can exist in four isomeric forms.

In this respect, in the structural formula (I) there are at least four asymmetric carbon atoms, but the absolute configuration of the terminal amino acid (Tyr or Phe) is the L- (this configuration being obtained using in the synthesis the suitable L-tyrosine or L-phenylalanine derivatives), and the absolute configuration of the two gem-diamino carbons is also fixed in that the fragment (VIII) is obtained from D-arginine and the fragment (X) is obtained from D-aspartic acid. Finally, the carbon atoms of the malonyl residues can be of R or S configuration. Consequently the compounds of formula (I) can be obtained and used in optically active form or in the form of an isomer mixture. When the synthesis process for the products of formula (I) leads to a mixture, this can if desired be resolved into the individual isomers by known resolution methods.

As already anticipated, the thymopentin with two retro-inverted peptide bonds has proved extremely stable to the action of plasmatic peptidase. In particular the lability of $[gArg^1,(R,S)mLys^2,gAsp^3,(R,S)mVal^4]TP5$ to enzymatic hydrolysis has been tested in parallel with both TP5 and $[gArg^1,(R,S)mLys^2]TP5$, using heparinized human plasma and incubating the three peptides separately at a concentration of about 30 nmoles/ml of plasma. The incubations were done at 37° C., and the withdrawn samples of the plasmatic mixture, of 100 μl each, were blocked at the various times by adding trifluoroacetic acid to the extent of 10%, followed by centrifuging at 10,000 g for 5 minutes. An aliquot of the supernatant was chromatographed under conditions suitable for showing the change in the peptide concentration at the various times. The enzymatic data obtained enabled the half life to be calculated, i.e. the time of incubation at 37° C. required for degrading 50% of the tested peptide, this being shown in the following Table I.

TABLE I

| Stability towards enzymatic hydrolysis in human plasma | |
|---|---|
| | (t/2 in minutes) |
| TP5 | ≈1.5 |
| $[gArg^1, (R, S)mLys^2]TP5$ | 22 |
| $[gArg^1, (R, S)mLys^2, gAsp^3, (R, S)mVal^4]TP5$ | >300 |

This considerably increased stability of the bi-retroinverted analogues relative to TP5 and the mono-retroinverted analogue has also been demonstrated using isolated enzymes (leucinaminopeptidase and carboxypeptidase).

The compound of Formula 1 has also shown considerable immunostimulating activity (greater than that of TP5 or of the mono-retro-inverted analogue) at extremely low doses. The immunostimulating activity of $[gArg^1,(R,S)mLys^2,gAsp^3, (R,S)mVal^4]TP5$ was tested in vivo compared with that of TP5 and of $[gArg^1,(R,S)mLys^2]TP5$.

Specifically, hemolysis plates (PFC) were used for the test, which was conducted by the method described by Jerne and Nordin. The test was carried out by intravenously administering to C3H/HeNCrlBr inbred male mice (Calco-Italia) of 10-12 weeks and about 25 g body weight an apyrogenic saline solution (0.2 ml) containing $1-2 \times 10^8$ red blood cells from sheep (SRBC). After two hours, groups each containing 3 mice were treated orally (intragastric tube) with 0.2 ml of saline solution (control) or with 0.2 ml of saline solution containing 1 ng of peptide. After 4 days the mice were killed and the spleen withdrawn and dissociated mechanically to separate the lymphocytes. The thus isolated lymphocytes were washed with minimum essential medium (MEM) ($3 \times 15$ ml) containing Earle's salts and then resuspended in the same medium (1 ml) at a final concentration of 150,000 cells. Each cell suspension (0.1 ml) was then diluted 1:100 with MEM, 100 μl of each dilution being doubly added to microplate wells containing 25 μl of MEM, 25 μl of a 10% solution of SRBC antigens and 25 μl of guinea pig complement at a final dilution of 1:64. The entire suspension was immediately transferred by capillarity from each well to superimposed slides. The slides, closed at their edges with paraffin, were then incubated in an environment temperature controlled at 37° C. for one hour.

At the end of this period the direct hemolysis plaques indicating the number of lymphocytes which secrete antibodies (PFC) are counted by a light contrast viewer. The antibodies displayed are of the IgM class, i.e. of primary antibody response. The results, expressed in % relative to the control, are given in Table II.

TABLE II

| Compound | Plaque formation % control |
|---|---|
| TP5 | 104 |
| TP5 $(RI_{1-2})$ | 112 |
| TP5 $(RI_{1-2})(RI_{3-4})$ | 219 |

In Table II, as elsewhere in this patent, "RI" indicates "retroinverso". TP5 $(RI_{1-2})$ consequently indicates the TP5 analogue retro-inverted at the 1-2 peptide bond, and TP5 $(RI_{1-2})$ $(RI_{3-4})$ indicates the thymopentin analogue retro-inverted both at the 1-2 bond and at the 3-4 bond.

Because of their biological characteristics, the peptides of the present invention are able to interfere with the body immune response, to substantially stimulate it when deficient. The compounds of the present invention are therefore therapeutically useful in treating a series of pathological states related to immunodeficiency. These include for example Di George's syndrome, characterised by a congenital absence of the thymus, or chronic or long-duration viral, fungal or microplasmatic infections. The present invention therefore further provides pharmaceutical compositions containing a therapeutically effective quantity of one or more of the compounds of formula (I).

For therapeutic use as immunostimulators or immunomodulators, the compounds of the present invention can be conveniently administered parenterally, orally or sub-lingually.

The formulations containing the new compounds can be prepared in the conventional manner by combining the active principle with an inert vehicle and possibly with suitably chosen conventional additives.

For oral or sub-lingual use, the compounds of the present invention can be administered in the form of tablets, capsules, drops, elixirs etc., prepared using conventional vehicles/excipients such as starch, sugar, water, alcohol etc. and possibly containing flavourings, stabilizers, preservatives, lubricants etc. For parenteral use, the chosen vehicle is sterile water for injections. Additives can be added in the known manner. The therapeutically effective daily dose varies according to the subject to be treated (weight, age and condition) and the method of administration. However, generally the compounds of the invention are active when administered at a daily dose of between 2 and 200 ng/kg. The pharmaceutical formulations of the present invention therefore contain the compounds of formula (I) in a quantity suitable to ensure correct daily dosage within the aforesaid range.

The following examples describe in detail some compounds representative of the present invention and their method of synthesis.

EXAMPLE 1

Synthesis of [gArg$^1$,(R,S)mLys$^2$,gAsp$^3$,(R,S)-mVal$^4$]TP5 acetate (the acetic acid addition salt of the compound of formula (I) where: R=H.)

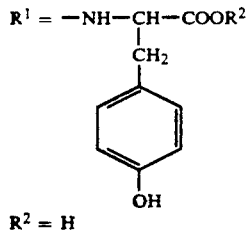

R$^2$ = H 1) (M)Val (2,2-dimethyl-5-isopropyl-1,3-dioxane-4,6-dione)

A solution of 2,2-dimethyl-1,3-dioxane-4,6-dione (Meldrum's acid) (14.4 g, 100 mmoles) in acetone (50 ml) containing pyridine (0.5 ml, 5 mmoles) and glacial acetic acid (0.3 ml, 5 mmoles) is stirred at ambient temperature for 6 hours, then evaporated to dryness. The residue is taken up in methanol (MeOH) (150 ml) and NaBH$_4$ (4.16 g, 110 mmoles) is added. After 15 minutes the MeOH volume is reduced to about 50 ml. H$_2$O (50 ml) is added and the solution adjusted to pH 3 by adding 3N HCl. The white precipitate obtained is recovered by filtration and dried in an oven (11.6 g, yield 63%). M.P. 98°–99° C.

$^1$H-NMR analysis confirms the assigned structure.

Chromatographic analysis carried out under the following conditions shows no trace of impurities:

Column: HiBar, Lichrosorb ® RP-18 (10μ)

Eluents: gradient from 0 to 40% of solution B in A within the first 20 minutes, from 40 to 80% of B in A within the next 10 minutes and then constant at 80% for a further 5 minutes (B=0.1% TFA in CH$_3$CN; A=0.1% TFA in 10% CH$_3$CN in H$_2$O)

Flow: 1.5 ml/min

Detection: U.V. 230 nm

Single peak T$_R$=18.27 min.

2) Fmoc—D—Asp(OBu$^t$)NH$_2$ [amide of N$^α$-fluorenyl-methoxycarbonyl-D-aspartic acid (β-tert-butyl ester)]

Some ammonium salt of 1-hydroxy-benzotriazole (HOBt.NH$_3$) (3.21 g, 20 mmoles) and a solution of N,N'-dicyclohexylcarbodiimide (DCC) (4,13 g, 20 mmoles) in N,N-dimethylformamide (DMF) are added to a solution of N$^α$-fluorenyl-methoxycarbonyl-D-aspartic acid (β-tertbutyl ester) [Fmoc—D—Asp(OBu$^t$)OH] (8.23 g, 20 mmoles) in DMF (60 ml), cooled to 0° C. and kept stirring in a nitrogen atmosphere. After about 60 minutes the ice bath is removed and stirring continued for a further 60 minutes at ambient temperature, the N,N'-dicyclohexylurea (DCU) which forms is filtered off and the solvent is removed by evaporation under reduced pressure. The crude reaction product is taken up in ethyl acetate (AcOEt) (150 ml), extracted with an aqueous 5% (w/v) NaHCO$_3$ solution (3×100 ml), and then with an aqueous saturated solution of NaCl (3×100 ml). The organic phase, dried over MgSO$_4$, is evaporated to dryness to give a white gelatinous mass which is triturated with H$_2$O and dried in an oven (7.8 g, yield 95%). M.P.=134°–136° C.

$^1$H-NMR analysis confirms the assigned structure.

Chromatographic analysis carried out under the conditions of step 1) shows a single peak with T$_R$=27.03 min.

3) H—D—Asp(OBu$^t$)NH$_2$ [amide of D-aspartic acid (β-tert-butyl) ester]

The product obtained in the preceding step (7.5 g, 18 mmoles) is treated for 60 minutes at ambient temperature in a nitrogen atmosphere, with a 80/20 DMF/diethylamine mixture (100 ml). After one hour the reaction mixture is evaporated to dryness, the residue is taken up in AcOEt (100 ml) and extracted with 0.1N HCl (3×70 ml). The aqueous phases are pooled and reduced to a volume of about 100 ml, then adjusted to pH 9 with a 10% (w/v) Na$_2$CO$_3$ solution and re-extracted with AcOEt (4×50 ml). The pooled phases are dried over MgSO$_4$ and evaporated under reduced pressure, to leave an oily residue which is purified by flash chromatography over silica, eluting with AcOEt and then with MeOH. 1.45 g of a yellowish oil are obtained (yield 44%).

$^1$H-NMR and mass analysis confirm the assigned structure.

HPLC analysis under the conditions of step 1) shows a single peak with T$_R$=6.52 min.

4) H-Tyr(Bu$^t$)OBu$^t$ (tert-butyl ester of L-tyrosine-O-tert-butylether)

A solution of ammonium formate (2.52 g, 40 mmoles) in MeOH (40 ml) and some 10% (w/w) Pd/C (3.5 g) are added to a solution of the tert-butyl ester of N$^α$-benzyloxycarbonyl-L-tyrosine-O-tert-butylether [Z-Tyr(-

Bu$^t$)OBu$^t$] [prepared by the method described in New Aspects in Physiological Antitumor Substances, Karger, Basel (1985) p. 33] (6.92 g, 16 mmoles) in MeOH (60 ml). The resultant suspension is kept stirring at ambient temperature under a nitrogen atmosphere for 30 minutes, and then filtered through celite, the solvent being removed by evaporation under reduced pressure. The oily residue obtained is taken up in a 10% (w/v) Na$_2$CO$_3$ solution (50 ml) and extracted with AcOEt (4×50 ml). The pooled organic phases are dried over MgSO$_4$ and the solvent removed by evaporation under reduced pressure. 3.6 g of a colourless oily product are obtained (yield 77%).

$^1$H-NMR analysis confirms the assigned structure.

HPLC analysis under the conditions of step 1) shows a single peak at T$_R$=20.90 min. Tlc (CMA) R$_f$=0.44.

5) HO—(R,S)mVal—Tyr(Bu$^t$)OBu$^t$ [tert-butyl ester of (R,S)-2-isopropyl-malonyl-L-tyrosine-O-tert-butylether]

(M)Val (1.012 g, 5.5 mmoles), N,O-bis-(trimethylsily)acetamide (BSA) (2.45 ml, 10 mmoles) and trimethylsilylchloride (TMSC) (0.634 ml, 5 mmoles) are added in succession to a solution of tert-butyl ester of L-tyrosine-O-tert-butylether [H-Tyr(Bu$^t$)OBu$^t$] (1.467 g, 5 mmoles) in tetrahydrofuran (THF) (25 ml).

The reaction is conducted in a nitrogen atmosphere at ambient temperature for 20 hours, then H$_2$O (50 ml) is added and the pH adjusted to 4 with citric acid. The reaction mixture is extracted with methylene chloride (3×50 ml), the organic phases are pooled, washed with water (50 ml), dried over MgSO$_4$, then evaporated under reduced pressure. 2.02 g of a colourless oil are obtained (yield 96%).

$^1$H-NMR and mass analysis confirm the assigned structure.

HPLC analysis under the conditions of step 1) shows a single peak with T$_r$=27.80 min.

6) H$_2$N—D—Asp(OBu$^t$)—(R,S)mVal—Tyr(Bu$^t$)OBu$^t$

A solution of HOBt (0.567 g, 3.96 mmoles) in DMF (3 ml) and a solution of DCC (0.73 g, 3.53 mmoles) in CH$_2$Cl$_2$ (5 ml) are added to a solution of the product obtained in step 5) (1.49 g, 3.53 mmoles) in CH$_2$Cl$_2$ (20 ml), cooled to 0° C. and kept stirring in a nitrogen atmosphere. After 60 minutes the ice bath is removed and stirring continued for a further 60 minutes. A solution is then added of the amide of D-aspartic acid the side chain carboxyl of which is protected as tert-butyl ester [H—D—Asp(OBu$^t$)NH$_2$] (0.62 g, 3.3 mmoles) in CH$_2$Cl$_2$ (7 ml), the reaction being conducted at ambient temperature for 20 hours.

The DCU which forms is filtered off, the solvent removed by evaporation under reduced pressure and the crude reaction product taken up in THF (30 ml). This is then cooled to −15° C. for 2 hours, the DCU precipitate removed by filtration, the solvent removed by evaporation under reduced pressure and the residue taken up in AcOET (75 ml). The solution is washed with an aqueous 5% (w/v) NaHCO$_3$ solution (3×50 ml), then with a saturated solution of NaCl (3×50 ml), with 0.1N HCl (3×50 ml) and finally with H$_2$O (3×50 ml). The organic phase is dried over MgSO$_4$, the solvent evaporated and the residue triturated with n-hexane (50 ml). A white solid is obtained (1.28 g, yield 65%) with M.P=113°-5° C.

$^1$H-NMR and mass analysis confirm the assigned structure.

HPLC analysis under the conditions of step 1) shows a single peak with T$_R$=29.21 min.

7) TFA.H—gAsp(OBu$^t$)—(R,S)mVal—Tyr(Bu$^t$)OBu$^t$

A solution of [[bis-(trifluoroacetoxy)iodo]benzene] (TIB) (0.807 g, 1.88 mmoles) in CH$_3$CN (5 ml) is added in small portions to a solution of the compound obtained in the preceding step (1.01 g, 1.706 mmoles) in a 2/1 CH$_3$CN/H$_2$O mixture (15 ml), kept stirring in a nitrogen atmosphere. After 3.5 hours at ambient temperature the solvent is removed and the residue triturated with a 1/1 ethyl ether/n-hexane mixture (20 ml). A white product (0.815 g, yield 70% is obtained with M.P=143°-145° C.

$^1$H-NMR and mass analysis confirm the assigned structure.

HPLC analysis under the conditions of step 1) shows a single peak with T$_R$=28.03 min.

8) Fmoc—D—Arg(Mtr)—NH$_2$ (amide of N$^\alpha$-fluorenylmethoxycarbonyl-N$^G$-(4-methoxy-2,3,6-trimethyl)-benzenesulphonyl-D-arginine)

A solution of the ammonium salt of 1-hydroxybenzotriazole (HOBt.NH$_3$) (3.0 g, 16.45 mmoles) in DMF (10 ml) and a solution of DCC (3.38 g, 16.45 mmoles) in DMF (10 ml) are added to a solution of N$^\alpha$-fluorenylmethoxycarbonyl-N$^G$-(4-methoxy-2,3,6-trimethyl)-benzenesulphonyl-D-arginine [Fmoc—D—Arg(Mtr)—OH] (10 g, 16.45 mmoles) in DMF (50 ml) cooled to 0° C. and kept stirring.

After about one hour the temperature is allowed to rise to ambient and stirring is continued for a further 60 minutes.

The DCU formed is then removed by filtration and the solvent is evaporated to obtain an oily residue which is taken up in AcOEt and washed firstly with an aqueous 5% (w/v) sodium bicarbonate solution (3×50 ml) and then with a saturated sodium chloride solution (3×50 ml).

The organic solution is dried over MgSO$_4$ and evaporated to dryness. The solid residue obtained is triturated with ethyl ether (Et$_2$O) (100 ml) to give a colourless powder (9.2 g, yield 93%). The product is characterised by a M.P. of 168°-172° C.

HPLC analysis under the conditions of step 1) shows a single peak with T$_R$=26.19 min.

9) HCl.H—D—Arg(Mtr)—NH$_2$ [hydrochloride of N$^G$-(4-methoxy-2,3,6-trimethyl)benzenesulphonyl-D-arginine amide]

A suspension of the compound obtained in step 8) (9 g, 15.5 mmoles) in a 80/20 DMF/diethylamine mixture (100 ml) is left stirring for one hour. The solvent is then removed by evaporation at reduced pressure, the residue is taken up in AcOEt (100 ml) and extracted with an aqueous 0.1N HCl solution (3×50 ml). The aqueous extracts are pooled, washed with further AcOEt (50 ml) and lyophilized several times to give a colourless flaky product (4.5 g, yield 80%).

The product has no precise melting point.

$^1$H-NMR analysis confirms the assigned structure.

HPLC analysis under the conditions of step 1) shows a single peak at T$_R$=12.69 min.

10) OEt—mLys(BOC)—OEt [ethyl ester of 2-(N-tert-butoxycarbonyl-4-butylamino)malonic acid]

Sodium metal (0.28 g, 12 mmoles) is dissolved in absolute ethyl alcohol (EtOH) (9 ml) under a stream of nitrogen. The mixture is heated to 60° C. and diethyl malonate (3.8 g, 24 mmoles) added dropwise. N-tert-butoxycarbonyl-4-chloro-butylamine (2.5 g, 12 mmoles) is gradually added at ambient temperature to the resultant solution. The reaction mixture is then stirred for 2 hours at ambient temperature and for 6 hours at reflux temperature, and then poured into a 1/1 (v/v) AcOEt/water mixture (100 ml). The separated organic phase is washed repeatedly with water and dried over MgSO₄.

The solvent is removed under vacuum at 100° C. leaving an oily crude product which is purified by reverse phase HPLC using RP-18 resin and eluting with an aqueous phase modified with CH₃Cn (45 vol %).

The desired compound is obtained (1.31 g) as pure product.

HPLC analysis under the conditions of step 1) shows a single peak at $T_R=27.08$ min.

TLC (n-hexane/AcOEt 70/30) $R_f=0.57$

11) HO—(R,S)mLys(BOC)—OEt [ethyl hemiester of 2-(N-tert-butoxycarbonyl-4-butylamino)malonic acid]

A solution of KOH (0.66 g, 9.97 mmoles) in EtOH (10 ml) is added drop by drop over two hours to a suspension of the compound obtained in the preceding step (3.48 g, 10.5 mmoles) in EtOH (15 ml) kept at 0° C. in a nitrogen atmosphere.

After 16 hours the reaction mixture is taken up in H₂O (70 ml), reduced to a small volume by evaporation under reduced pressure and extracted with Et₂O (3×50 ml). The aqueous phase is then acidified with 1N HCl to pH 3 and further extracted with AcOEt (3×50 ml). The organic extracts are pooled, washed with a saturated aqueous NaCl solution and dried over Mg SO₄.

On evaporating the solvent under reduced pressure the desired product is obtained as a transparent oil (2.64 g, yield 83%).

¹H-NMR analysis confirms the assigned structure.

HPLC analysis under the conditions of step 1) shows a single peak at $T_R=19.58$ min.

TLC (CMA) $R_f=0.58$

12) H₂N—D—Arg(Mtr)—(R,S)mLys(BOC)—OEt (ethyl ester of (R,S) [2-(N-tert-butoxycarbonyl)-4-butylamine]-malonyl-N^G-(4-methoxy-2,3,6-trimethlbenzenesulphonyl)-D-arginine amide)

A solution of HOBt (0.76 g, 6.3 mmoles) in DMF (10 ml) and a solution of DCC (1 g, 4.85 mmoles) in DMF (5 ml) are added to a solution of the compound of the preceding step (1.47 g, 4.85 mmoles) in DMF (15 ml) cooled to 0° C. and kept stirred under a nitrogen atmosphere.

After one hour the temperature is allowed to rise to ambient and stirring is continued for a further 60 minutes. A solution of the compound of step 9) (1.86 g, 4.4 mmoles) in DMF (15 ml) containing triethlamine (TEA) (0.612 ml, 4.4 mmoles) is then added. The reaction is conducted at ambient temperature for 20 hours, after which an excess of DCC (0.2 g, 0.97 mmoles) is added and stirring continued for a further 4 hours.

The DCU which forms is then removed by filtration, the DMF is removed by evaporation under reduced pressure, the residue is taken up in THF (20 ml) and left cooled to −15° C. overnight, after which it is refiltered and evaporated to dryness.

The oily residue obtained is taken up in AcOEt (70 ml) and the organic solution washed in sequence with an aqueous 5% solution of sodium bicarbonate (3×50 ml), with an aqueous saturated solution of NaCl (3×50 ml), with a 0.1N aqueous HCl solution (3×50 ml) and again with the aqueous saturated solution of NaCl (3×50 ml). The organic phase is then dried over MgSO₄ and evaporated. The oily residue obtained is triturated with hexane, to finally give a finely divided white powder (2.26 g, yield 76%). The product has a M.P. of 148°–149° C.

¹H-NMR and mass analysis confirm the assigned structure.

HPLC analysis under the conditions of step 1) shows a single peak at $T_R=23.38$ min.

TLC (CMA) $R_f=0.4$

13) H₂N—D—Arg(Mtr)—(R,S)mLys(BOC)—OH [N^α-(R,S)-malonyl-2-(N-butoxycarbonyl)-4-butylamine]-N^G-(4-methoxy-2,3,6-trimethylbenzenesulphonyl)-D-arginine amide)

A solution of KOH (0.204 g, 3.63 mmoles) in absolute EtOH (5 ml) is added drop by drop over a period of 1½ hours to a solution of the compound obtained in the preceding-step (2.21 g, 3.3 mmoles) in absolute EtOH (20 ml) cooled to 0° C. and kept under nitrogen. After 16 hours the reaction mixture is diluted with water (50 ml), evaporated to a small volume and extracted with Et₂O (3×50 ml). The aqueous phase is acidified with 0.1N HCl to pH 3 and then further extracted with AcOEt (3×50 ml). The organic extracts are pooled, dried over MgSO₄ and evaporated. An oily residue is obtained (1.97 g, yield 93%), the structure of which is confirmed by ¹H-NMR and mass analysis. HPLC analysis conducted by the standard procedure of step 1) shows a double peak due to the pair of diastereoisomers at $T_R=20.02$ and 20.52 min. TLC (CMA) $R_f=0.13$ and 0.19.

14) H₂N—D—Arg(Mtr)—(R,S)mLys(BOC)—gAsp-(OBu^t)—(R,S)mVal—Tyr(Bu^t)—OBu^t

A solution of HOBt (35 mg, 0.24 mmoles) in DMF (0.3 ml) and a solution of DCC (45.4 mg, 0.22 mmoles) in DMF (0.3 ml) are added to a solution of the compound obtained in the preceding step (141 mg, 0.22 mmoles) in DMF (0.5 ml) after cooling to 0° C., in a nitrogen atmosphere.

After 60 minutes the temperature is allowed to rise to ambient and the solution left stirring for a further 60 minutes. A solution of the compound obtained in step 7) (136 mg, 0.2 mmoles) in DMF (0.9 ml) containing TEA (28 μl, 0.2 mmoles) is then added. After stirring for 20 hours, the DCU which forms is filtered off and the filtrate evaporated to dryness. The solid residue obtained is taken up in AcOEt (7 ml), washed with an aqueous 5% (w/v) NaHCO₃ solution (3×5 ml), then with a saturated solution of NaCl (3×5 ml), with 0.1N HCl (3×5 ml) and finally with water (3×5 ml). The organic phase is dried over MgSO₄ and evaporated to dryness. The desired product is obtained (187 mg, yield 79%).

¹H-NMR and mass analysis confirm the assigned structure.

HPLC analysis displays no trace of impurities and shows a single peak at $T_R=31.84$ min.

15) TFA.H—gArg(Mtr)—(R,S)mLys(BOC)—gAsp-(OBu^t)—(R,S)mVal—Tyr(Bu^t)—OBu^t

The compound of the preceding step (170 mg, 0.14 mmoles) is dissolved in a mixture containing CH₃CN (1.5 ml), H₂O (1 ml) and DMF (0.5 ml), kept an ambient temperature under a nitrogen atmosphere. A solution of TIB (66.2 mg, 0.154 mmoles) in CH₃CN (0.5 ml) is then added. After 4 hours, the reaction mixture is evaporated to dryness, and the residue taken up in MeOH (75 ml) and evaporated to dryness several times. A slightly yellow coloured vitreous product is obtained (130 mg, yield 73%) the structure of which is confirmed by mass analysis, and which shows a purity exceeding 93% on HPLC analysis ($T_R=32.03$ min).

16) AcOH.H—gArg—(R,S)mLys—gAsp—(R,S)-mVal—Tyr—OH ([gArg¹,(R,S)mLys²,gAsp³,(R,S)mVal⁴]TP5 acetate)

The entire product of the preceding step (130 mg, ≈0.1 mmoles) is treated for 20 minutes at ambient temperature in a nitrogen atmosphere with a freshly prepared solution containing trifluoroacetic acid (TFA), trifluoromethanesulphonic acid (TFMSA) and 1,2-ethanedithiol (EDT) (TFA/TFMSA/EDT 89/1/10) (20 ml).

After 20 minutes the reaction mixture is cooled to 0° C. and TEA (0.3 ml, 1.44 mmoles) is added drop by drop, after which it is evaporated to dryness under a nitrogen stream.

The residue is taken up in $H_2O$ (50 ml), extracted with $Et_2O$ (30 ml) and the ether phase is counter-extracted with $H_2O$ (20 ml).

The two aqueous phases are pooled and extracted with $Et_2O$ (3×30 ml) and then evaporated under reduced pressure. The oily residue obtained is purified by ion exchange chromatography in a column (15×0.9 cm) packed with CM-Sephadex C-25 (2 g) and developed with a linear gradient in ammonium acetate at pH 4.4, from 0.15 to 0.6M in 8 hours, at a flow of 0.7 ml/min.

The fractions containing the desired product are pooled, concentrated to a small volume under reduced pressure and lyophilized. 47.2 mg of product are obtained (yield 64%).

¹H-NMR and mass analysis confirm the product structure, while HPLC analysis confirms it purity (under the standard conditions of step 1), showing a single peak at $T_R = 8.28$ min.

We claim:

1. A compound of formula (I)

$$R-NH-CH-NH-CO-CH-CO- \atop {\underset{\underset{\underset{NH_2}{|}}{\underset{C=NH}{|}}}{\underset{NH}{|}}\atop (CH_2)_3} \quad {\underset{NH_2}{|}\atop (CH_2)_4}$$

(I)

$$-NH-CH-NH-CO-CH-CO-R^1 \atop {\underset{\underset{COOH}{|}}{\underset{CH_2}{|}}} \quad {\underset{\underset{CH_3}{|}}{\underset{CH-CH_3}{|}}}$$

where
R is hydrogen or an acyl radical, and
$R^1$ is an $-OR^2$ group or an $$-NH-CH-COOR^2 \atop {\underset{\underset{\text{(phenyl ring with } R^3)}{|}}{\underset{CH_2}{|}}}$$

group where
$R^2$ is a hydrogen atom or a $C_1-C_6$ linear or branched chain alkyl radical, a $C_3-C_6$ linear or branched chain alkenyl or alkynyl radical, or a $C_7-C_{12}$ aryl-alkyl or alkyl-aryl radical, and
$R^3$ is a hydrogen atom or a hydroxyl group, and the corresponding pharmaceutically acceptable salts of acid or basic addition.

2. A compound as claimed in claim 1, wherein R is hydrogen or a metabolically labile acyl radical, $R^1$ is as heretofore defined and $R^2$ is hydrogen.

3. A compound as claimed in claim 2, wherein R is hydrogen.

4. A compound as claimed in claim 3, wherein $R^1$ is a $$-NH-CH-COOR^2 \atop {\underset{\underset{\text{(phenyl ring with } R^3)}{|}}{\underset{CH_2}{|}}}$$

in which $R^2$ is a hydrogen atom and $R^3$ is as heretofore defined.

5. A compound as claimed in claim 4, chosen from [gArg¹,(R,S)mLys²,gAsp³,(R,S)mVal⁴]TP5 and its salts of addition.

6. A pharmaceutical composition which contains a compound of claim 1 in a therapeutically effective amount and a pharmaceutically acceptable carrier.

7. A method of stimulating a deficient immune system which comprises administering to a host having a deficient immune system a therapeutically effective amount of the compound of claim 1.

8. A method of stimulating a deficient immune system which responds to the immunostimulating activity spectrum of thymopentin which comprises administering a therapeutically effective amount of the compound of claim 1 to a host having such a deficient immune system.

* * * * *